(12) United States Patent
Shipp et al.

(10) Patent No.: US 8,066,714 B2
(45) Date of Patent: Nov. 29, 2011

(54) INSTRUMENTATION FOR DISTRACTION AND INSERTION OF IMPLANTS IN A SPINAL DISC SPACE

(75) Inventors: Kenneth S. Shipp, Collierville, TN (US); Mitchell J. Campbell, Louisville, KY (US); Richard Evan Chen, Memphis, TN (US)

(73) Assignee: Warsaw Orthopedic Inc., Warsaw, IN (US)

( * ) Notice: Subject to any disclaimer, the term of this patent is extended or adjusted under 35 U.S.C. 154(b) by 1362 days.

(21) Appl. No.: 11/378,897

(22) Filed: Mar. 17, 2006

(65) Prior Publication Data
US 2007/0233153 A1    Oct. 4, 2007

(51) Int. Cl.
*A61F 2/00* (2006.01)

(52) U.S. Cl. ............................. 606/99; 606/105; 606/914

(58) Field of Classification Search ................ 606/86 A, 606/86 B, 86 R, 90, 100, 99, 206, 207, 208, 606/209, 914–916, 105; 29/278, 255, 237, 29/270
See application file for complete search history.

(56) References Cited

U.S. PATENT DOCUMENTS

| | | | | |
|---|---|---|---|---|
| 2,219,907 A * | 10/1940 | Ross | ................................ | 279/93 |
| 2,260,048 A * | 10/1941 | Newell | ........................... | 411/552 |
| 3,486,505 A | 12/1969 | Morrison | | |
| 3,661,411 A * | 5/1972 | Flick | .............................. | 403/348 |
| 3,860,209 A * | 1/1975 | Strecker | ........................ | 410/116 |
| 4,386,603 A | 6/1983 | Mayfield | | |
| 4,736,738 A | 4/1988 | Lipovsek et al. | | |
| 4,756,638 A * | 7/1988 | Neyret | ........................... | 403/261 |
| 4,893,801 A * | 1/1990 | Flinn | ................................. | 269/6 |
| 4,898,161 A | 2/1990 | Grundei | | |
| 4,955,885 A | 9/1990 | Meyers | | |
| 5,122,130 A | 6/1992 | Keller | | |
| 5,156,305 A * | 10/1992 | Eyre | .............................. | 222/327 |
| 5,161,787 A * | 11/1992 | Hobday | ............................. | 269/6 |
| 5,192,327 A | 3/1993 | Brantigan | | |
| D334,524 S * | 4/1993 | Pinkney | ........................... | D8/73 |
| 5,235,966 A | 8/1993 | Jamner | | |
| 5,375,309 A * | 12/1994 | Dunn | .............................. | 29/237 |
| 5,431,658 A | 7/1995 | Moskovich | | |
| 5,505,732 A | 4/1996 | Michelson | | |
| 5,597,260 A * | 1/1997 | Peterson | ....................... | 403/319 |

(Continued)

FOREIGN PATENT DOCUMENTS

EP          260925 A1 *   3/1988

(Continued)

OTHER PUBLICATIONS

Synthes, SynCage Surgical Technique, Mathys Medical Ltd. Osteosynthesis, pp. 1-24; Guterstrasse 5, P.O. Box, CH-2544 Bettlach, Switzerland.

*Primary Examiner* — Eduardo C Robert
*Assistant Examiner* — Jan Christopher Merene (57) ABSTRACT

Instruments for inserting an implant in a space between adjacent bony portions include upper and lower guide members and a drive assembly between the spreaders with an implant positioned forwardly of the drive assembly. The drive assembly is coupled to a handle assembly, and the handle assembly is operable to move the implant forwardly between the guide members to position the implant in a space between the bony portions. The handle assembly includes a mounting portion to which the drive assembly is mounted and an actuating portion operable to effect linear movement of the drive assembly.

20 Claims, 9 Drawing Sheets

U.S. PATENT DOCUMENTS

| | | | |
|---|---|---|---|
| 5,599,279 A | | 2/1997 | Slotman et al. |
| 5,620,291 A | * | 4/1997 | Hayes et al. ............... 411/552 |
| 5,626,435 A | * | 5/1997 | Wohlhuter ................. 403/348 |
| 5,697,889 A | | 12/1997 | Slotman et al. |
| 5,716,362 A | * | 2/1998 | Treacy ......................... 606/87 |
| 5,722,977 A | | 3/1998 | Wilhelmy |
| 5,913,605 A | * | 6/1999 | Jusselin et al. ............... 37/451 |
| 5,944,658 A | | 8/1999 | Koros et al. |
| 6,004,326 A | | 12/1999 | Castro et al. |
| 6,083,225 A | | 7/2000 | Winslow et al. |
| 6,096,038 A | | 8/2000 | Michelson |
| 6,174,311 B1 | | 1/2001 | Branch et al. |
| 6,179,873 B1 | | 1/2001 | Zientek |
| 6,224,599 B1 | | 5/2001 | Baynham et al. |
| 6,224,607 B1 | | 5/2001 | Michelson |
| 6,261,296 B1 | | 7/2001 | Aebi et al. |
| 6,270,498 B1 | | 8/2001 | Michelson |
| 6,292,142 B1 | * | 9/2001 | Pittman ................. 343/700 MS |
| 6,332,887 B1 | | 12/2001 | Knox |
| 6,336,766 B1 | * | 1/2002 | De Villele .................. 403/348 |
| 6,338,475 B1 | * | 1/2002 | Ping ............................. 269/6 |
| 6,395,034 B1 | | 5/2002 | Suddaby |
| 6,436,101 B1 | | 8/2002 | Hamada |
| 6,478,800 B1 | | 11/2002 | Fraser et al. |
| 6,514,260 B1 | | 2/2003 | Zdeblick et al. |
| 6,565,574 B2 | | 5/2003 | Michelson |
| 6,595,995 B2 | | 7/2003 | Zdeblick et al. |
| 6,610,065 B1 | | 8/2003 | Branch et al. |
| 6,635,060 B2 | | 10/2003 | Hanson et al. |
| 6,641,582 B1 | | 11/2003 | Hanson et al. |
| 6,652,533 B2 | | 11/2003 | O'Neil |
| 7,147,399 B2 | * | 12/2006 | Viscount et al. ............. 403/349 |
| 7,661,215 B2 | * | 2/2010 | Okamoto ...................... 40/620 |
| 2001/0010001 A1 | | 7/2001 | Michelson |
| 2002/0082695 A1 | | 6/2002 | Neumann |
| 2002/0116009 A1 | | 8/2002 | Fraser et al. |
| 2002/0120334 A1 | * | 8/2002 | Crozet ...................... 623/17.11 |
| 2002/0138078 A1 | | 9/2002 | Chappuis |
| 2002/0177897 A1 | | 11/2002 | Michelson |
| 2003/0028197 A1 | | 2/2003 | Hanson et al. |
| 2003/0045884 A1 | | 3/2003 | Robie et al. |
| 2003/0083664 A1 | | 5/2003 | Rogers et al. |
| 2003/0130737 A1 | | 7/2003 | McGahan et al. |
| 2003/0149438 A1 | | 8/2003 | Nichols et al. |
| 2003/0187448 A1 | | 10/2003 | Michelson |
| 2003/0195517 A1 | | 10/2003 | Michelson |
| 2003/0195520 A1 | | 10/2003 | Boyd et al. |
| 2003/0225416 A1 | | 12/2003 | Bonvallet et al. |
| 2004/0002758 A1 | | 1/2004 | Landry et al. |
| 2004/0011161 A1 | * | 1/2004 | Gmeilbauer ..................... 81/9.3 |
| 2004/0037635 A1 | * | 2/2004 | Viscount et al. ............. 403/348 |
| 2004/0106927 A1 | * | 6/2004 | Ruffner et al. ................. 606/90 |
| 2004/0128814 A1 | * | 7/2004 | Esson et al. ................... 29/237 |
| 2004/0220582 A1 | * | 11/2004 | Keller ........................... 606/99 |
| 2004/0225295 A1 | | 11/2004 | Zubok et al. |
| 2005/0119665 A1 | * | 6/2005 | Keller ........................... 606/99 |
| 2005/0165408 A1 | * | 7/2005 | Puno et al. .................... 606/99 |
| 2006/0195097 A1 | * | 8/2006 | Evans et al. ................... 606/61 |
| 2007/0123904 A1 | * | 5/2007 | Stad et al. ..................... 606/99 |

FOREIGN PATENT DOCUMENTS

| | | |
|---|---|---|
| EP | 0 531 710 A2 | 3/1993 |
| EP | 0 637 439 A1 | 2/1995 |
| EP | 1 295 578 A2 | 3/2003 |
| EP | 1 323 396 A2 | 7/2003 |

* cited by examiner

INSTRUMENTATION FOR DISTRACTION AND INSERTION OF IMPLANTS IN A SPINAL DISC SPACE

BACKGROUND

The repair and reconstruction of bony structures is sometimes accomplished by directly fixing adjacent bony portions to each other, such as by a plate. In other instances, bone growth inducing material can be introduced between the adjacent bony portions, which over time results in a solid bony connection. In some patients, the adjacent bony portions are not sufficiently strong to maintain their patency as the bone heals or as the bone grows between the adjacent structures through the bone growth inducing material. In such cases, grafts, cages, artificial joints and other implants have been provided to engage the adjacent bony structures to provide additional stability.

One problem, among others, with such implants is associated with positioning the implant in the space between adjacent bony portions. Insertion can be difficult or time consuming if the bony portions are spaced too close together, or if the adjacent tissue, nerves or vasculature impedes access to or placement of the implant in the space between the bony portions. Furthermore, maintenance of distraction of the space during insertion of the implant requires additional instruments in the space or in the operative approach to the space which can make the procedure more invasive and impede access and visibility during implant insertion.

SUMMARY

The invention provides instruments that facilitate placement of implants between adjacent bony portions, such as vertebrae of a spinal column.

According to one aspect, a system for implant delivery to a space between adjacent bony portions includes a handle assembly, a pair of opposed elongate guide members, and a drive member assembly. The handle assembly includes a pistol-grip type assembly formed by a mounting portion and an actuating portion rotatably coupled together. The pair of opposed elongate guide members are rotatably coupled to the mounting portion, and each of the guide members includes a distal end adapted to be positioned in the space. A spreader is disposed between the guide members and the drive member assembly is coupled to the handle assembly and the spreader. The drive member assembly includes a drive member axially movable towards the guide member distal ends upon rotational actuation of the handle assembly actuating portion.

According to another aspect, a system for implant delivery to a space between adjacent bony portions includes an implant positionable in the space and a handle assembly including a mounting portion and an actuating portion. A pair of opposing guide members are coupled to the mounting portion, and each of the guide members includes a body extending along an insertion axis between a distal end positionable in the space and a proximal end. The guide members each include an outer surface and an opposite guide surface with the guide surfaces oriented toward one another.

In one form the system includes a spreader positioned between the pair of guide members and the implant is positioned distally of the spreader. The system includes a drive member assembly coupled to the handle assembly and the spreader. The drive member assembly includes a drive member linearly movable along the insertion axis by operation of the actuating portion of the handle assembly. The drive member includes a distal coupling portion having a non-circular cross-sectional shape, and the spreader includes a central bore for receiving the distal coupling portion of the drive member. The central bore includes a proximal portion having a shape that corresponds to the non-circular cross-sectional shape of the distal coupling portion and a distal portion having a shape limiting rotation of the coupling portion to a rotated position upon rotation of the drive member. The coupling portion cannot pass through the proximal portion of the central bore when in the rotated position.

In another form the system includes a drive member assembly coupled to the handle assembly that includes a drive member extending toward the implant between the guide members. The drive member is mounted to the mounting portion of the handle assembly. The drive member assembly includes a driving tab coupled to the actuating portion of the handle assembly. The driving tab and the actuating portion are normally biased to a first position and are movable toward a second position to obliquely orient the driving tab relative to the insertion axis and engage the drive member with the driving tab to linearly advance the drive member along the insertion axis relative to the guide members as the actuating portion is moved toward the second position.

In another form, the system includes a drive member assembly coupled to the handle assembly that includes a drive member extending toward the implant between the guide members. The drive member is moveable along the insertion axis in response to movement of the actuating portion. At least a portion of the guide surfaces of the guide members are concavely curved in a direction transversely oriented to the insertion axis, and at least a portion of the implant is convexly curved and moveable with the drive member along the concavely curved portions of the guiding surfaces.

In another form, the guide members are spring biased relative to the handle assembly and pivotally coupled thereto so that the distal ends of the guide members are biased toward one another.

In another form, the guide members include distal support portions positionable in the space in contact with the bony portions that include a pair of axially extending support members spaced by a width that is at least as great as the width of a contact area of the implant with the bony portions between the support members.

These and other aspects can be discerned from the following written description and accompanying figures.

DESCRIPTION OF THE ILLUSTRATED EMBODIMENTS

For the purpose of promoting an understanding of the principles of the invention, reference will now be made to the illustrated embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

An instrument is provided for inserting implants into a space between adjacent bony portions to support the adjacent bony portions. The inserter instrument can be used with any type of bone support implant, such as artificial joints, spacer devices, and fusion devices, for example. The implants can be made from bone material or any suitable biocompatible metal, plastic, or other material. The implants can also be made from combinations of materials, and include multiple components fixed to or movable relative to one another. In one application, the inserter instrument is employed in spinal surgical procedures for inserting an impacted bone implant in the disc space between adjacent vertebrae. In another application, the inserter instrument guides placement of a threaded implant between vertebrae.

The adjacent bony portions can include a first vertebra and an adjacent second vertebra separated by a disc space and/or one or more removed vertebral bodies. The space between the vertebrae provides a space for insertion of an implant between the adjacent bony portions. The inserter instrument can be used in various approaches to the disc space in spinal surgical procedures, including posterior, postero-lateral, transforaminal, lateral, antero-lateral, oblique, and anterior approaches. The inserter can also be used in approaches to various regions of the spine, including the sacral, lumbar, thoracic and cervical regions. It is contemplated that the inserter instrument can have application in surgical procedures other than spinal surgical procedures to facilitate insertion of an implant between adjacent bony portions.

Figure 1:
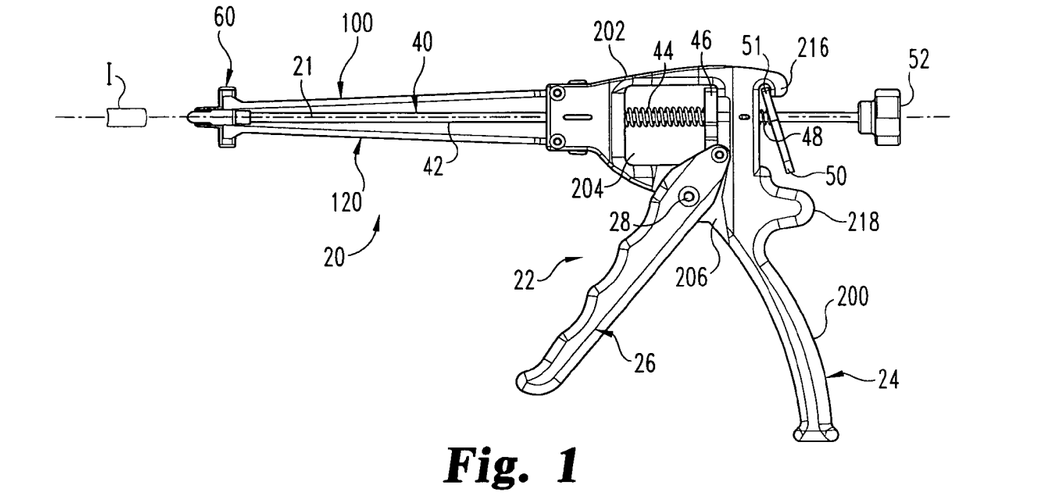
FIG. 1 is an elevation view of one embodiment inserter instrument and implant.

In FIG. 1 an inserter instrument 20 is shown. Inserter instrument 20 includes a handle assembly 22 with a drive member assembly 40 extending therethrough and coupled thereto. Guide members 100, 120 are coupled to handle assembly 22 and extend distally therefrom along an insertion axis 21. Drive member assembly 40 also extends along insertion axis 21 and includes a distal portion that is positionable in the space between upper and lower guide members 100, 120. The distal end of drive member assembly 40 can engage a spreader 60 positioned between guide members 100, 120. An implant I can be positioned forwardly or distally of spreader 60. Implant I can be engaged by spreader 60 to facilitate in maintaining the positioning of implant I between guide members 100, 120 as implant I is moved along insertion axis 21. Spreader 60 is moveable distally or forwardly by manipulating drive member assembly 40 relative to handle assembly 22 to advance drive member assembly 40 forwardly along insertion axis 21 and toward distal ends of guide members 100, 120. Other embodiments contemplate that drive member assembly 40 can be engaged directly to implant I with or without a spreader 60.

The proximal ends of guide members 100, 120 are pivotally attached to handle assembly 22, facilitating loading of the implant I and placement of the distal ends of guide members 100, 120 adjacent one another for positioning in the spinal disc space. As spreader 60 pushes implant I distally between guide members 100, 120, the distal ends of guide members 100, 120 can separate and thus apply a distraction force to the adjacent vertebrae. The vertebrae are distracted sufficiently to receive implant I since the final distraction height is determined by either or both of the height of implant I and the height of the spreader between the distal ends of guide members 100, 120.

It should be understood that the terms "upper" and "lower" refer to the orientation of the elements of the instruments in the Figures as shown relative to the surgeon when grasping handle assembly 22, i.e. upper means away from the pistol grip portion of handle assembly 22 and lower means toward the pistol grip portion of handle assembly 22. The instruments can be rotated or repositioned such that, for example, the pistol grip portion can extend upwardly, axially, and/or guide member 100 is positioned below guide member 120. In addition, distal and proximal refer to orientations of the instrument relative to the surgeon as the inserter instrument 20 is being employed during surgery, i.e. distal is more toward the implantation location in the patient and proximal is more toward the surgeon.

Figure 3:
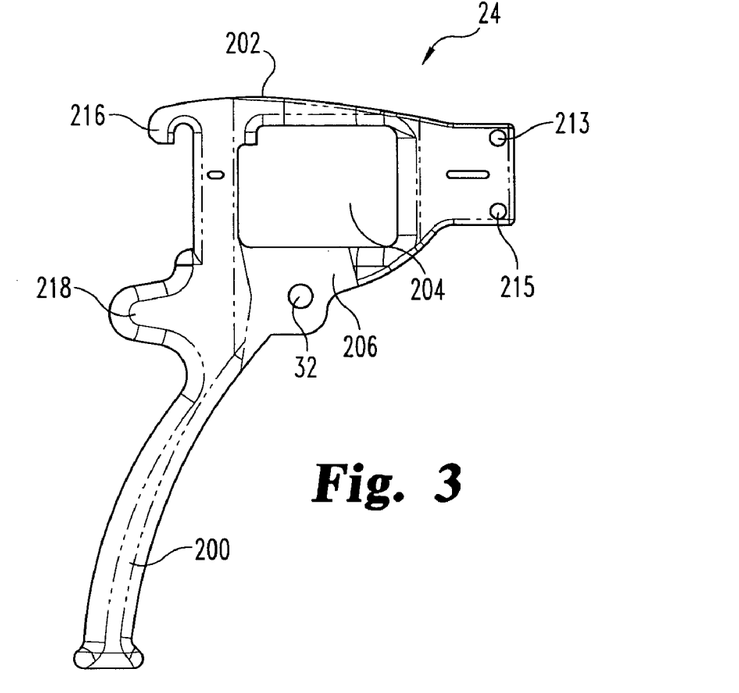
FIG. 3 is an elevation view of a mounting portion of a handle assembly of the inserter instrument of FIG. 1.
Figure 4:
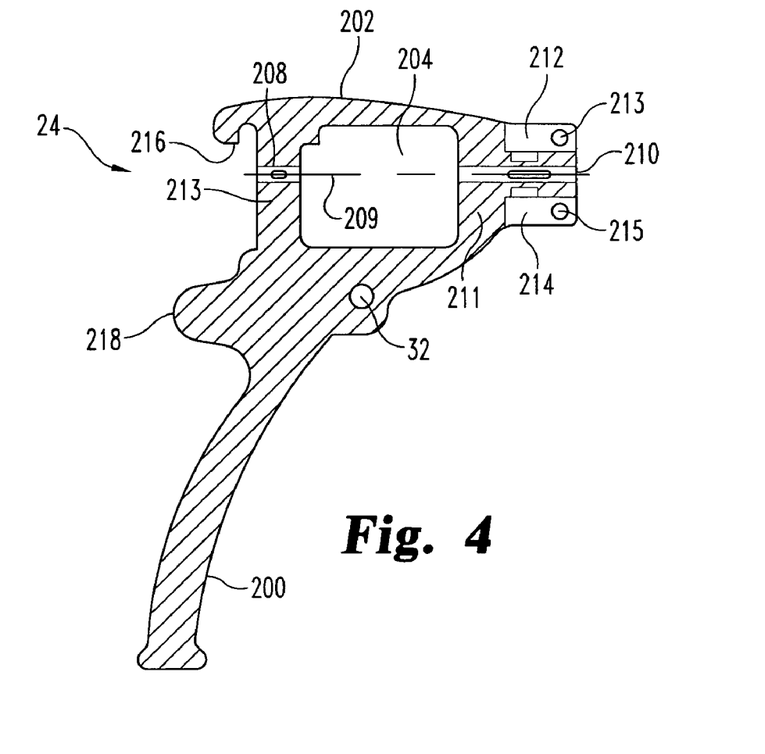
FIG. 4 is a sectional view of the mounting portion of FIG. 3.

Further details of the handle assembly 22 of inserter instrument 20 will be discussed with further reference to FIGS. 3-6. Handle assembly 22 includes a mounting portion 24 through which a drive member 42 of drive member assembly 40 extends and to which guide members 100, 120 are mounted. Handle assembly 22 further includes an actuating portion 26 pivotally coupled to mounting portion 24 with a handle pin 28 extending through aligned apertures 30, 32. As shown in FIGS. 3-4, mounting portion 24 includes a fixed handle part 200 and an upper mounting part 202. Mounting part 202 includes a central window 204 extending therethrough transversely to insertion axis 21, and a recessed part 206 below window 204 to receive actuating portion 26.

Figure 5:
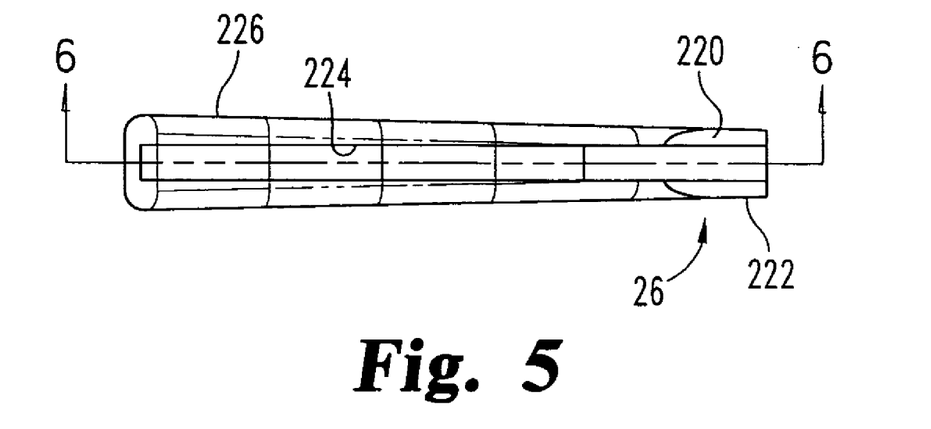
FIG. 5 is an elevational view of an actuating portion of the handle assembly of the inserter instrument of FIG. 1.
Figure 6:
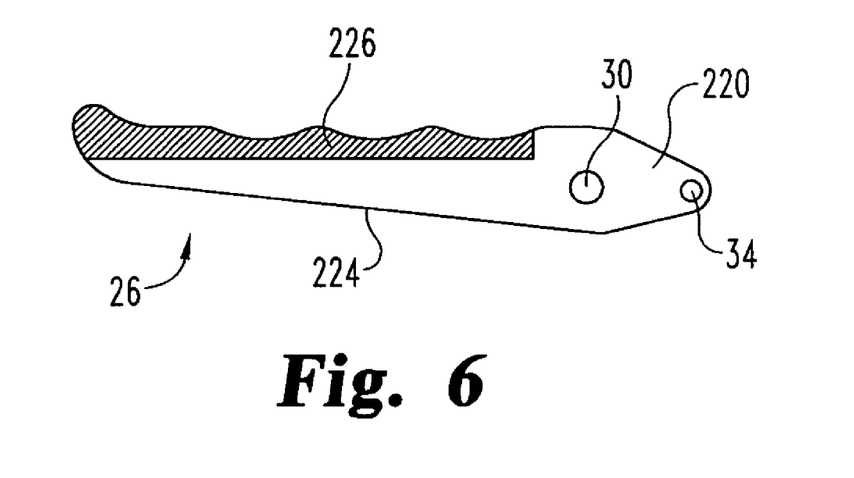
FIG. 6 is a section view along line 6-6 of FIG. 5.

As shown in FIGS. 5 and 6, actuating portion 26 includes a gripping part 226 with a slot 224 extending therealong and opening opposite of gripping part 226. Gripping part 226 can include an undulating surface therealong to facilitate comfortable positioning of the fingers of the user thereagainst. A pair of ears 220, 222 extends from gripping part 226 and includes apertures 30 therethrough. Ears 220, 222 also include inner tab apertures 34, which are discussed further below. Ears 220, 222 are sized to locate inner tab apertures 34 in window 204 when actuating portion 26 is pivotally coupled to mounting portion 24 with handle pin 28 in apertures 30, 32 as shown in FIG. 1.

Referring back to FIGS. 3-4, fixed handle part 200 is convexly curved away from actuating portion 26 to comfortably reside in the palm and thumb region of the user's hand. A proximally directed projecting part 218 can extend along the upper side of the user's hand when positioned about fixed handle part 200. Together, fixed handle part 200 and actuating portion 26 provide a pistol-grip type arrangement where squeezing action of actuating portion 26 can effect linear translation of drive member 42 and thus spreader 60 and implant I along insertion axis 21 toward the implantation location in the patient.

Upper mounting part 202 includes a proximal bore 208 through a proximal wall 213 and a distal bore 210 through a distal wall 211, each of which extends along drive member axis 209. Drive member axis 209 can be parallel to and extend along insertion axis 21. Bores 208, 210 are in communication with window 204 at respective ends thereof. The distal wall 211 of upper mounting part 202 includes first and second guide member engaging recesses 212, 214 for receiving guide members 100, 120 therein, respectively. Distal bore 210 is located between recesses 212, 214. Each of the recesses 212, 214 includes an aperture 213, 215, respectively, for receiving a respective one of the guide member coupling pins 36, 37 with a proximal end portion of the adjacent guide member 100, 120 positioned in the respective recess 212, 214. Upper mounting part 202 further includes a proximally extending retaining hook 216 that extends from proximal wall 213 and engages a portion of drive member assembly 40, as discussed further below.

Figure 7:
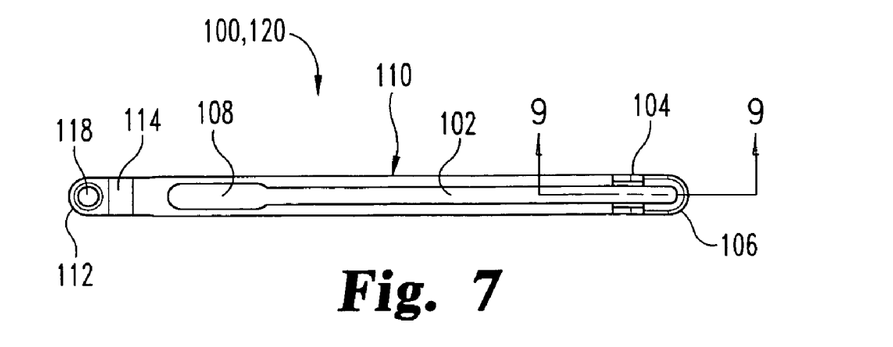
FIG. 7 is a plan view of a guide member of the inserter instrument of FIG. 1.
Figure 8:
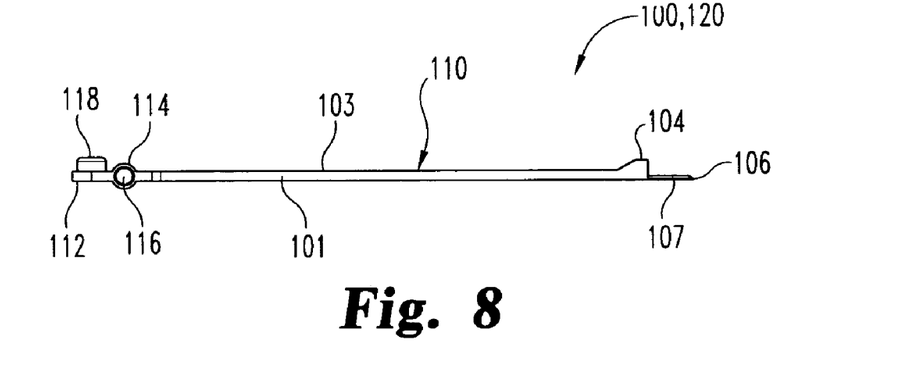
FIG. 8 is an elevational view of the guide member of FIG. 7.
Figure 9:
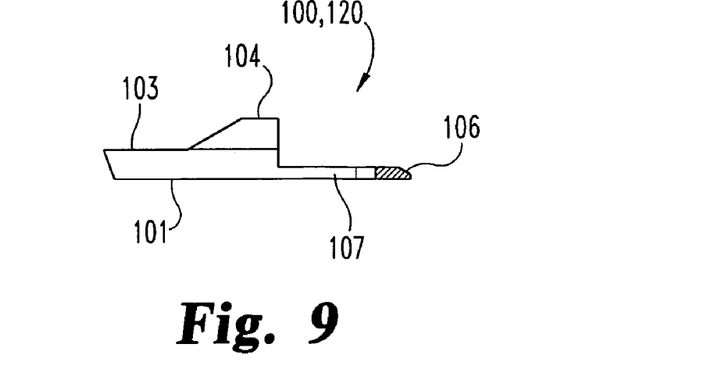
FIG. 9 is a section view along line 9-9 of FIG. 7.

Referring also to FIGS. 7-9, guide members 100, 120 will be discussed further, it being understood that the guide members 100, 120 can be configured the same or similarly to one another. Guide members 100, 120 extend distally from handle assembly 22, and define a path for insertion of the implant between the adjacent bony portions, such as between vertebrae. Guide members 100, 120 each include a body 110 extending from a proximal end 112 to a distal end 106. Body 110 can be provided with an elongated guide slot 102 extending therethrough along a central axis of body 110. Guide slot 102 opens along a guide surface 101 and an opposite outer surface 103 of body 110. Guide slot 102 extends from a location adjacent proximal end 112 to distal end 106. Guide slot 102 is shown as being enclosed at each end by body 110; however, it is understood that one or both ends of slot 102 could open at distal end 106 and proximal end 112. Guide slot 102 includes an enlarged proximal end portion 108 for passage of the enlarged outer end of spreader 60, as discussed further below. The remaining distal portion of guide slot 102 is sized to slidingly receive a portion of spreader 60 as it is moved therealong.

Guide members 100, 120 can be provided with an abutment member 104 adjacent distal end 106 projecting from outer surface 103 for contacting the adjacent bony structure to limit the insertion depth of guide members 100, 120 into the space between the adjacent bony portions. A support portion 107 of guide member 100 extends distally from abutment member 104 and into the space between the adjacent bony portions, forming an extension of and being co-planar with guide surface 101.

Guide members 100, 120 also include a connecting hub 114 adjacent proximal end 112. Connecting hub 114 defines a bore 116 therethrough to receive a respective one of the guide member coupling pins 36, 37 therethrough to couple the guide member 100, 120 in the respective recess 212, 214 of mounting part 202 of handle assembly 22. Proximally of the pivotal coupling locations of the guide members 100, 120, there can be positioned a spring 122, 124 (FIG. 2) in the respective recess 212, 214 between guide member 100, 120 and mounting part 202. Springs 122, 124 push outwardly on the proximal ends 112 of guide members 100, 120 to bias the distal ends 106 toward one another about the pivotal coupling location with mounting part 202. Outer surface 103 of guide members 100, 120 can include outwardly extending projections 118 adjacent proximal end 112 to facilitate access to apply manual forces to pivot the distal ends 106 of guide members 100, 120 away from one another.

When assembled to handle assembly 22, the guide surfaces 101 of guide members 100, 120 are oriented toward one another. Support portions 107 can extend along an adjacent surface of the adjacent bony portion to facilitate insertion of the implant I into the space between the adjacent bony portions. Support portions 107 also contact the adjacent bony portions to distribute a spreading or distraction force thereto. The spreading or distraction force can be applied to the adjacent bony portions by separating guide members 100, 120 as the implant I and spreader 60 are distally advanced between guide members 100, 120. Support portions 107 further protect the adjacent vertebral endplate as implant I is positioned in the space between the adjacent bony portions, and facilitate insertion of implant I in the desired position in the space between the adjacent bony portions.

Figure 10:
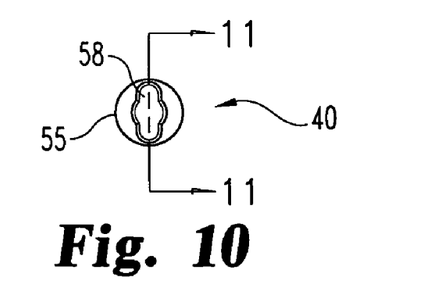
FIG. 10 is an end view of a drive member of the inserter instrument of FIG. 1.
Figure 11:
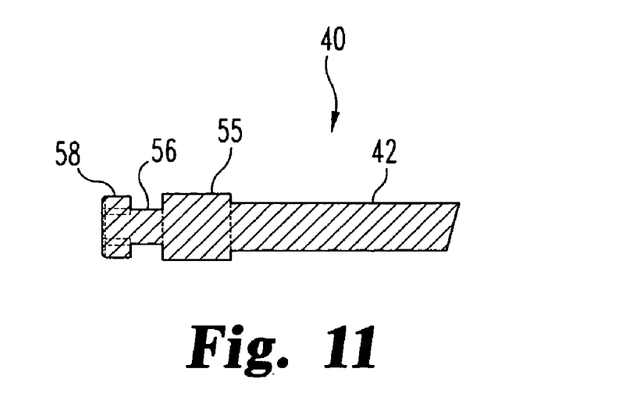
FIG. 11 is a section view of a distal portion of the drive member along line 11-11 of FIG. 10.
Figure 12:
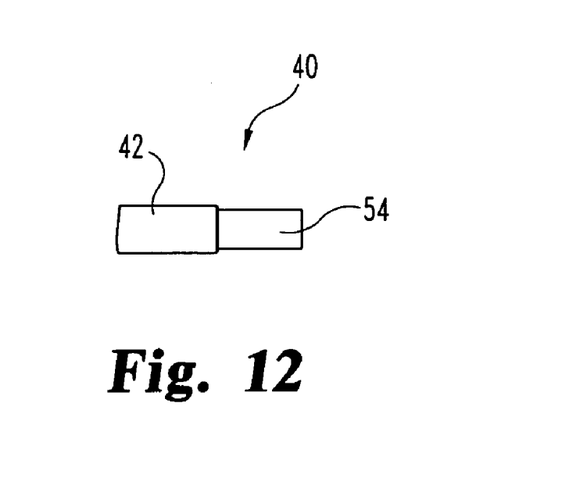
FIG. 12 is an elevational view of a proximal portion of the drive member.
Figure 13:
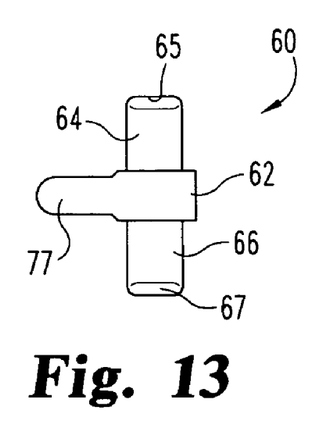
FIG. 13 is a side elevational view of a spreader of the inserter instrument of FIG. 1.
Figure 14:
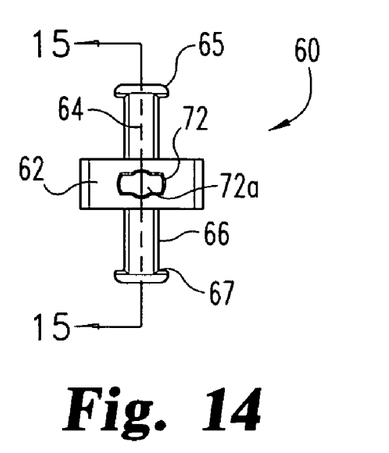
FIG. 14 is a rear elevational view of the spreader of FIG. 13.
Figure 15:
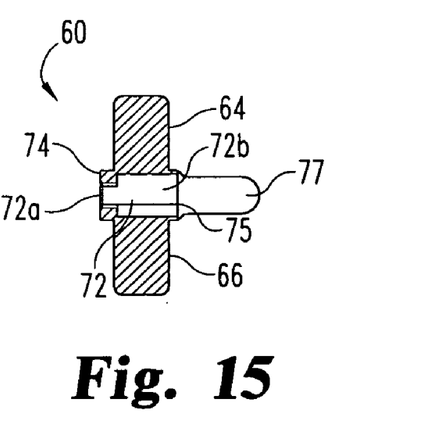
FIG. 15 is a section view along line 15-15 of FIG. 14.
Figure 16:
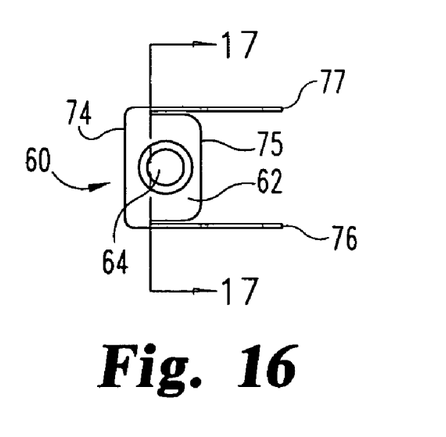
FIG. 16 is a top plan view of the spreader of FIG. 13.

In FIGS. 10-12 portions of drive member 42 are shown. Drive member 42 has a proximal end shaft 54 for receiving and engaging a knob 52 positioned thereover as shown in FIG. 1. The distal end of drive member 42 includes an engaging structure that includes a distal coupling portion 58 and a hub 55 proximally of coupling portion 58. Coupling portion 58 and hub 55 are connected by a reduced size linking portion 56 extending therebetween. Hub 55 can include a cylindrical shape and coupling portion 58 can include an irregular shape for connecting with an implant as discussed further below. In the illustrated embodiment, coupling portion 58 includes a cross-sectional shape orthogonally to the longitudinal axis of drive member 42 that, as shown in FIG. 10, includes a series of three overlapping circles, of which the middle circular portion has a greater diameter than the outer circular portions.

Figure 2:
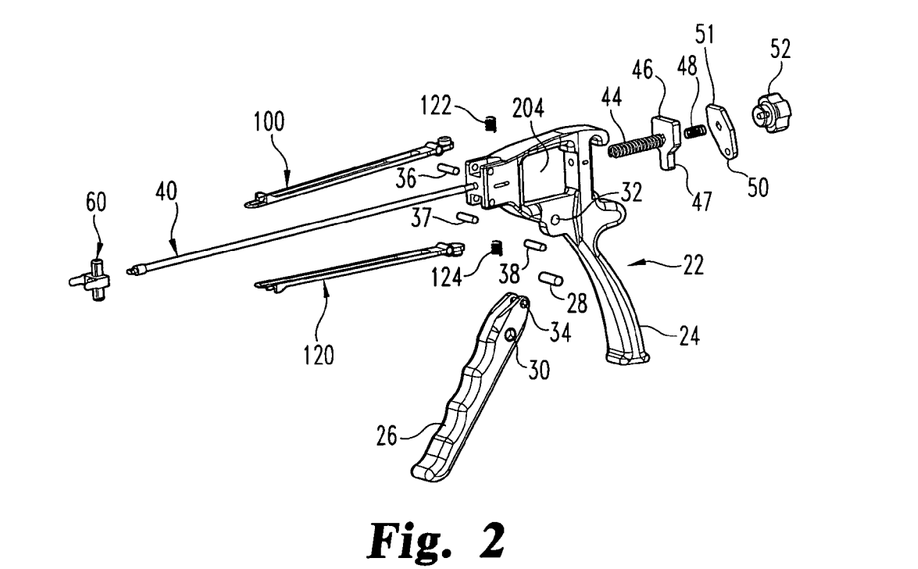
FIG. 2 is an exploded perspective view of the inserter instrument of FIG. 1.

As shown in FIGS. 1-2, drive member 42 is engaged to mounting part 202 of handle assembly 22 through proximal bore 208 and distal bore 210 lying along drive member axis 209. Drive member 42 extends through window 204, and includes a drive tab biasing spring 44 therearound in window 204. Spring 44 includes a distal end contacting a proximally facing surface of distal wall 211 in window 204, and a proximal end contacting driving tab 46 to bias it toward proximal wall 213. Driving tab 46 is positioned about and pivotal relative to drive member 42, and includes a lower end 47 positioned between ears 220, 222 of actuating portion 26. Ears 220, 222 define driving tab aperture 34 and include driving tab pin 38 extending therebetween proximally of driving tab 46 and in contact with lower end 47 thereof. Drive member assembly 40 further includes a locking tab 50 proximally of upper mounting part 202 positioned about and pivotal relative to drive member 42. Locking tab 50 includes an upper end 51 in contact with retaining hook 216. A locking tab spring 48 is positioned about drive member 42 between a proximally oriented surface of proximal wall 213 of upper mounting part 202 and locking tab 50. Locking tab 50 is thus biased proximally along drive member 42 so that upper end 51 normally contacts retaining hook 216 and locking tab 50 is pivoted in an oblique orientation relative to drive member 42 so that it is normally engaged thereto.

In the locked position of FIG. 1, driving tab 46 is biased in a generally orthogonal orientation to drive member 42, and locking tab 50 is biased to an oblique orientation relative to drive member 42 so that it is positively engaged to drive member 42 to maintain the relative axial positioning thereof. Drive member 42, spreader 60 and implant I can be linearly advanced along guide members 100, 120 in the direction of insertion axis 21 by pivoting actuating portion 26 toward fixed handle part 200. This in turn displaces lower end 47 of driving tab 46 to compress spring 44 and pivot driving tab 46 to positively engage drive member 42, creating axial distal displacement of drive member 42 as actuating portion 26 is depressed. When actuating portion 26 is released, spring 44 returns driving tab 46 to its orthogonal orientation and proximally displaces it along drive member 42, while locking tab 50 remains frictionally engaged to drive member 42 to maintain its relative axial position along guide members 100, 120. When actuating portion 26 is squeezed again, drive member 42 is incrementally distally advanced along insertion axis 21 by the pivoting movement of driving tab 46.

When it is desired to release drive member 42 so it can freely slide in mounting part 202 of handle assembly 22, the lower end of locking tab 50 can be depressed against the bias of spring 48 to move locking tab 50 toward an orthogonal or near orthogonal orientation relative to drive member 42, allowing drive member 42 to freely or nearly freely slide through locking tab 50 so that drive member 42 can be displaced proximally or distally along insertion axis 21. When locking tab 50 is released, spring 48 returns locking tab 50 to its pivoted or oblique orientation relative to drive member 42, as shown in FIG. 1, where locking tab 50 re-engages drive member 42 to maintain its positioning.

In FIGS. 13-17, spreader 60 is shown. Spreader 60 can be attached adjacent coupling portion 58 of drive member 42 and is movable along guide members 100, 120 as drive member 42 is moved therealong. Spreader 60 includes a central body 62 having an upper wing 64 and a lower wing 66 extending therefrom in opposite directions from one another. Wings 64, 66 can each include an outer end 65, 67 sized to prevent passage through the distal portion of slot 102, while being sized to pass through proximal portion 108 of slot 102 to facilitate assembly and disassembly with guide members 100, 120.

Figure 17:
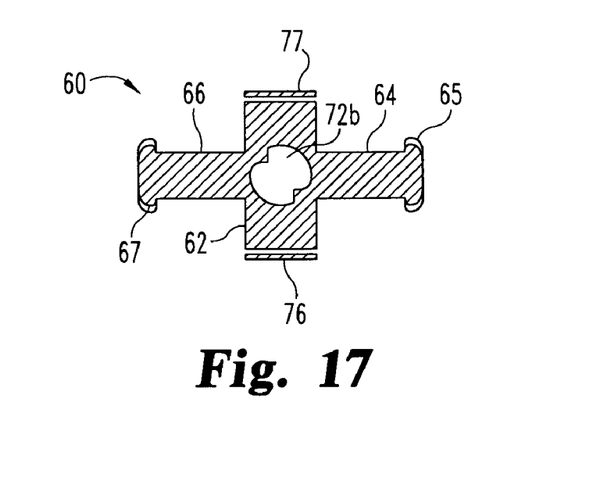
FIG. 17 is a section view along 17-17 of FIG. 16.

Spreader 60 also include a bore 72 that extends centrally through central body 62 along insertion axis 21, and can open at the proximal end 74 and distal end 75 of central body 62. Bore 72 can include a proximal portion 72a that has a shape that corresponds to the shape of coupling portion 58 to allow passage of coupling portion 58 therethrough in a predetermined orientation. Bore 72 also includes a distal portion 72b as shown in FIG. 17 having an interrupted circular shape that permits coupling portion 58 of drive member 42 to be rotated a quarter turn about its longitudinal axis when coupling portion 58 is positioned in distal portion 72b of bore 72. Accordingly, drive member 42 can be quickly locked and unlocked with spreader 60 by inserting coupling portion 58 through proximal portion 72a of bore 72 into distal portion 72b of bore 72, and then rotating drive member 42 with knob 52 a quarter turn so that coupling portion 58 cannot pass through proximal portion 72a of bore 72. In the locked position, hub 55 abuts against proximal wall 74, and the wall portion defining proximal portion 72a of bore 72 is located in recess 56 of drive member 42.

Spreader 60 further includes leading or distal end 75 that includes one or more engaging members 76, 77. Engaging members 76, 77 are engageable along the sides of implant I positioned forwardly of spreader 60, and facilitate in maintaining implant I in position between guide members 100, 120 as it is advanced therealong. Engaging members 76, 77 can be in the form of distally extending flanges that are spaced apart and generally parallel to one another. Other embodiments contemplate other forms for engaging members 76, 77, including non-parallel flanges, or members that can extend into and engage the implant.

In one embodiment, it is contemplated that implant I is selected from a set of implants having various widths, heights and/or angulation between its upper and lower surfaces. The implant of the appropriate height can be selected to provide a height that corresponds to a desired restored disc space height or separation distance between bony portions when implanted. If vertebral motion is desired, implant I can be an artificial disc implant. Implant I can include upper and/or lower anchoring members extending therefrom for engagement with an adjacent vertebra or vertebrae to maintain a positioning of implant I in the disc space. In one embodiment, the anchoring members may be in the form of elongated blades, spikes, keels, teeth, or ridges that are alignable along and positionable through the adjacent slots of guide members 100, 120. The guide members 100, 120 can be modified so that the slots are open at the distal end of the guide members 100, 120 to allow passage of the anchoring member therethrough. The anchoring members can be moved along guide members 100, 120 and into engagement with the adjacent vertebrae or bony portions as implant I is positioned in the space therebetween.

Implant I can be positionable between guide members 100, 120 when one of the guide members is moved away from the other. Spreader 60 is positioned between guide members 100, 120 with wings 64, 66 aligned with enlarged proximal end portions 108 of the slots 102. Guide members 100, 120 are then pivoted so that wings 64, 66 extending through portions 108. Implant I can be positioned between guide members 100, 120 forwardly or distally of spreader 60. The pivoting coupling arrangement of guide members 100, 120 with handle assembly 22 and the spring bias of guide members 100, 120 allows the distal ends of guide members 100, 120 to initially be positioned adjacent one another with implant I captured between guide members 100, 120 and in contact with or adjacent to the inner guide surfaces 101 of guide members 100, 120.

The distal ends of guide members 100, 120 are biased for positioning adjacent one another when implant I and spreader 60 are adjacent the proximal ends of guide members 100, 120. This provides a low profile arrangement that allows positioning of support portions 107 in the disc space or space between bony portions, even if the space is collapsed or has re-collapsed due to removal of distraction. Abutment members 104 are positionable in contact with the adjacent vertebral bodies or bony portions, preventing over-insertion of guide members 100, 120 into the space therebetween. In the illustrated embodiment, abutment members 104 are orthogonally oriented to the insertion axis 21, aligning guide members 100, 120 for implant insertion approach along or parallel to, for example, the sagittal plane in an anterior approach for spinal procedures. In another embodiment, abutment members 104 are obliquely oriented to the central longitudinal axis of guide members 104 to facilitate placement of guide members 100, 120 in an approach obliquely oriented to, for example, the sagittal plane in spinal procedures.

Implant I can be advanced distally between guide members 100, 120 by squeezing handle assembly 22 to pivot actuator portion 26, thereby linearly and incrementally advancing drive member 42 between guide members 100, 120 along insertion axis 21. Spreader 60 and implant I are thus also distally advanced between guide members 100, 120 along the insertion axis toward the implantation location. As implant I and spreader 60 are distally advanced, the guide members 100, 120 are spread apart or separated from one another. This separation causes support portions 107 to separate and exert a distraction force on the vertebral endplates or other bony portions, separating the vertebrae or other bony portions a sufficient distance to accommodate implant I therebetween.

When implant I is positioned in the spinal disc space or other space between bony portions, wings 64, 66 are aligned with abutment members 104 that are in contact with the adjacent bony portions. Support portions 107 are positioned between the inserted implant I and the adjacent bony portions, making manual withdrawal of inserter instrument 20 from the disc space difficult. Wings 64, 66 each include a distal end wall that extends from body 62 of spreader 60 to the enlarged outer end 65, 67 of the respective wing 64, 66.

Drive member 42 can be linearly advanced with handle assembly 22 to position wings 64, 66 in contact with the adjacent bony portions. Slots 102 extend through abutment members 104 providing an avenue for displacement of spreader 60 relative to guide members 100, 120. As driver member 42 is further linearly and distally actuated, wings 64, 66 press against the adjacent bony portions, causing guide members 100, 120 to displace proximally relative to spreader 60 until the wings contact the distal ends of slots 102. The distal end walls of wings 64, 66 can act on the bony portions to displace guide members 100, 120 proximally, withdrawing support portions 107 from the space between implant I and the adjacent bony portions or vertebral endplates. This allows inserter instrument 20 to be readily withdrawn from the operative site without twisting or impaction, which could disrupt implant positioning in the disc space.

Figure 18:
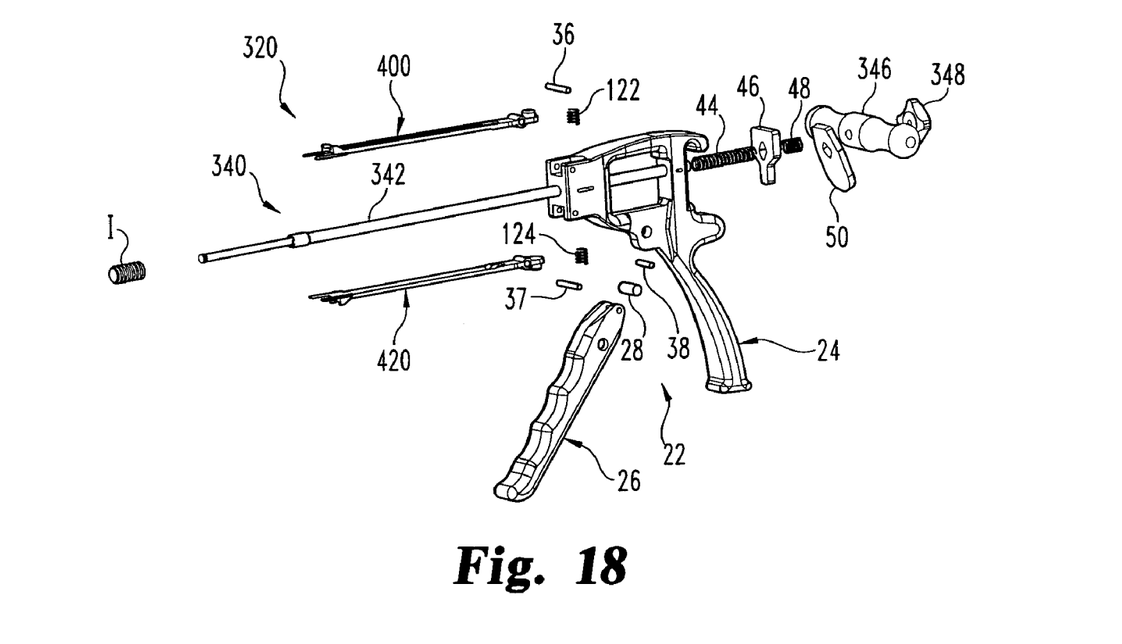
FIG. 18 is an exploded perspective view of another embodiment inserter instrument and implant.

Referring now to FIG. 18, there is shown another embodiment inserter instrument 320. Inserter instrument 320 has several elements that are the same as inserter instrument 20 discussed above, and such like elements will not be specifically discussed with respect to inserter instrument 320, it being understood that any discussion above with regard to these like elements is also applicable to inserter instrument 320. Inserter instrument 320 primarily differs from inserter instrument 320 in that inserter instrument 320 does not include a spreader although such is not precluded, the distal configuration of the drive member 342 and the proximal handle assembly of drive member assembly 340 differs from drive member assembly 40, and guide members 400, 420 include configuration that differs in part from that of guide members 100, 120.

In FIG. 18 implant I is shown as a threaded device that is rotated between adjacent bony portions to threadingly engage the adjacent bony portions and provide a platform or scaffold therebetween for bony fusion. Inserter instrument 320 is particularly suited for implantation of threaded implants or other device that contemplate rotation during insertion into the space between adjacent bony portions. Inserter instrument 320 includes a drive assembly 340 engaged to handle assembly 22 and extending therefrom between upper and lower guide members 400, 420. Upper and lower guide members 400, 420 can be pivotally coupled to and biased relative to handle assembly 22 in a manner similar to that discussed above with respect to guide members 100, 120 and handle assembly 22.

Figure 19:
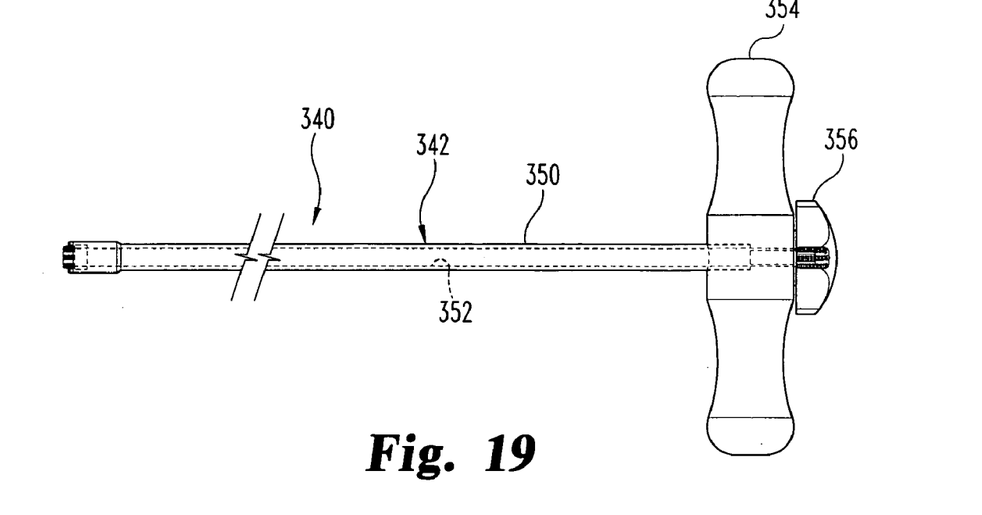
FIG. 19 is an elevation view of a driver member of the inserter instrument of FIG. 18.
Figure 20:
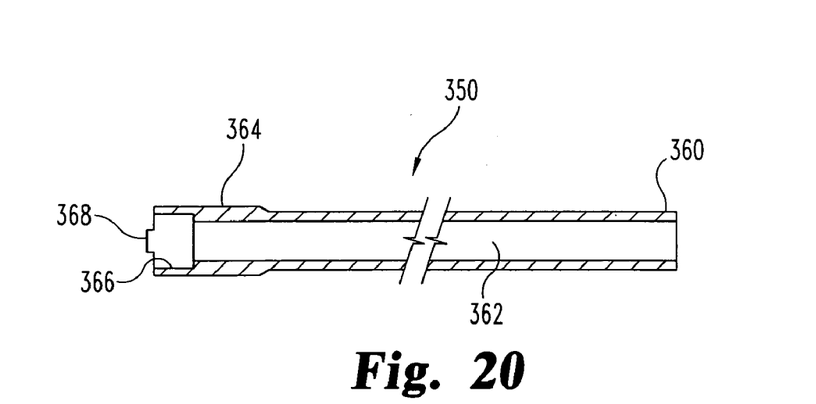
FIG. 20 is a sectional view of an outer member of the driver member of FIG. 19.

As shown in FIG. 19, drive assembly 340 includes a drive member 342 in the form of an outer shaft 350 extending about an inner shaft 352. Outer shaft 350 includes a drive handle 354 engaged to the proximal end thereof, and inner shaft 352 includes an engaging handle 356 engaged to the proximal end thereof proximally of handle 354. In FIG. 20, outer shaft 350 is shown in longitudinal section view, and includes a central passage 362 extending between a proximal end 360 and a distal projecting portion 364. Passage 362 includes an enlarged distal portion 366 opening at the distal end of outer shaft 350 in projecting portion 364. In addition, outer shaft 350 includes distal projecting members 368 extending distally therefrom.

Figure 21:
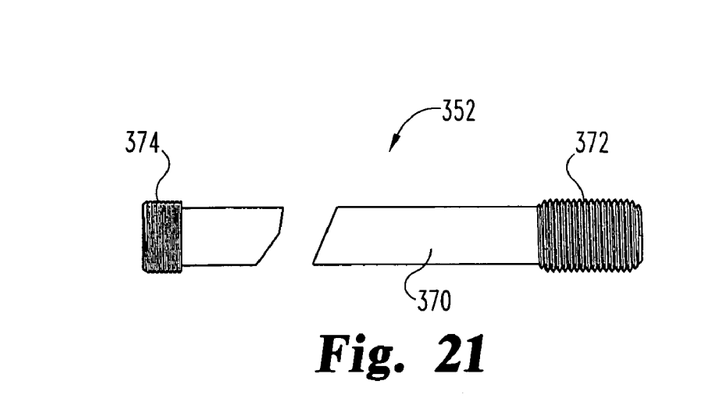
FIG. 21 is an elevational view of an inner member of the driver member of FIG. 19.

Inner shaft 352 is shown further in FIG. 21, and includes an elongated body 370 extending between a proximal threaded member 372 and a distal threaded member 374. When assembled with outer shaft 350, proximal threaded member 372 is proximal of proximal end 360, and distal threaded member 374 is received at least partially in enlarged distal portion 366 of central passage 362. Engaging handle 356 can be threadingly engaged to proximal threaded member 372.

Distal threaded member 374 is threadingly engageable within a threaded receptacle of implant I by grasping engaging handle 356 and turning it to rotate inner shaft 352 and thus distal threaded member 374 to threadingly engage it to implant I. This in turn draws implant I toward outer shaft 350, and implant I can be provided with one or more receptacles adjacent its threaded opening to receive distal projecting members 368. Distal projecting members 368 can interface with implant I to allow a driving force to be applied to rotate implant I through rotation of outer shaft 350 with driving handle 354 engaged to proximal end 360 of outer shaft 350.

Implant I can be linearly advanced along guide members 400, 420 by manipulating handle assembly 22 as discussed above with respect to inserter instrument 20. However, when implant I in FIG. 18 reaches the adjacent bony portions, it is rotated to advance between and engage the adjacent bony portions. Outer shaft 350, and thus implant I, can be rotated by grasping and rotating driving handle 354 about the longitudinal axis of drive member 342 to rotate implant I. Since inner shaft 352 is engaged to implant I it also rotates with outer shaft 350. Locking tab 56 can be pivoted to an orthogonal, unlocked positioned relative to drive member 342 to facilitate rotational movement of drive member 342, although it is also contemplated that locking tab 56 can remain in its locked position and the frictional locking forces can be overcome manually to rotate drive member 342. Since outer shaft 350 and inner shaft 352 rotate together when engaged to implant I, distal threaded member 374 does not tighten or unloosen relative to implant I when drive member 342 is rotated with drive handle 354. Inner shaft 352 can be disengaged from the implanted implant I by grasping drive handle 354 and rotating inner shaft 352 with drive handle 356 to unthread distal threaded member 374 from implant I while projecting members 368 engage the implant to maintain its positioning in the disc space until inner shaft 352 is disengaged from implant I.

Referring now to FIGS. 22-25, further details regarding guide members 400, 420 will be discussed, it being understood that the upper and lower guide members can be substantially identical to one another but oriented with their inner guide surfaces 401 toward one another. Guide members 400, 420 include an elongated central slot 402 extending between a proximal end 412 and a distal end 406. Proximal end 412 can include a connecting hub 414 and an outwardly extending projection 418 configured and arranged in a manner similar to that discussed above with respect to connecting hub 114 and projection 118 of guide members 100, 120.

Figure 22:
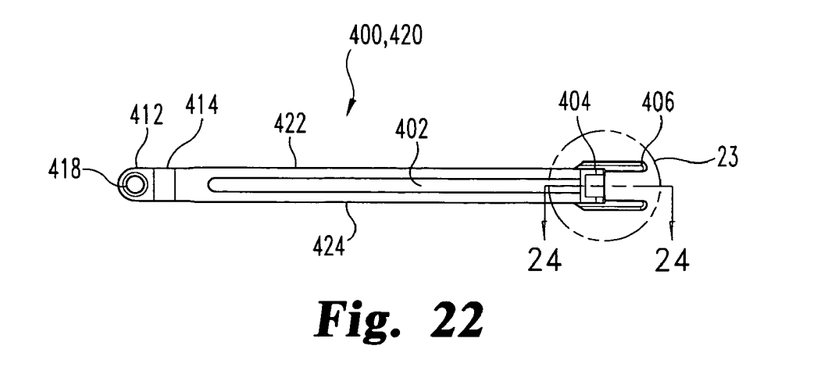
FIG. 22 is a top plan view of a guide member of the inserter instrument of FIG. 18.
Figure 23:
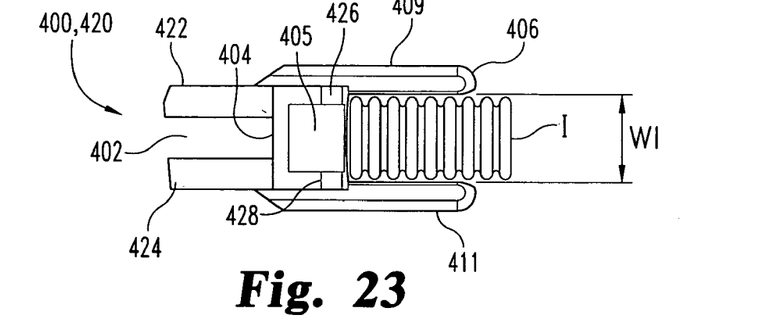
FIG. 23 is an enlarged view of a distal portion of the guide member of FIG. 22 in region 23.
Figure 24:
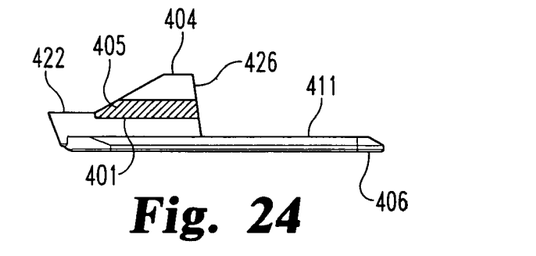
FIG. 24 is a section view along line 24-24 of FIG. 22.

Slot 402 separates guide member 400, 420 into a pair of side-by-side rails 422, 424 extending from a location adjacent proximal end 412 to an abutment member 404 adjacent distal end 406. Abutment member 404 is positionable against the adjacent bony portion when inserter instrument 320 is in use. Abutment member 404 includes a pair of outwardly extending sloped arms 426, 428 connected by linking portion 405 extending between the pair of arms.

Figure 25:
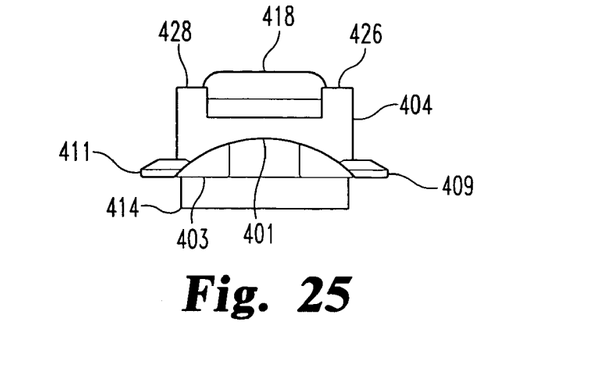
FIG. 25 is an end elevational view of the guide member of FIG. 22.

Guide members 400, 420 further include a support portion 407 extending distally from abutment member 404 that is positionable in the space between and in contact with the adjacent bony portions to effect distraction and separation of the bony portions as implant I is advanced distally along guide members 400, 420 and inserted between the bony portions. Support portion 407 includes first and second support members 409, 411 separated by a width W1. Width W1 can be greater than the implant width where it contacts the adjacent bony portions so that implant I can be threadingly advanced between support members 409, 411 while support members 409, 411 contact the adjacent bony portions. In addition, guide rails 422, 424 and abutment member 404 can include a guide surface 401 extending therealong that includes a concave curvature transverse to the insertion axis of implant I and oriented to accommodate passage of the convexly curved implant I therealong as it is advanced into the space between the bony portions. Proximal end portion 412 can include a flat surface 403, as shown in FIG. 25, that transitions to the convexly curve guide surface 401 adjacent the proximal end of slot 402.

As implant I is guided between guide members 100, 120 or guide members 400, 420 into the space between the adjacent bony portions, the positioning of implant I is controlled in the upper and lower direction (cephalad/caudal directions in spinal procedures) by contact of guide surfaces of the guide members with implant I. The guide surfaces align implant I with the space between the adjacent bony portions. The lateral positioning of implant I along the guide members is controlled by engagement of implant I with engaging members 76, 77 of spreader 60 or with the guide surfaces of the guide members so that implant I does not slip out from between guide members where it might contact or damage tissue, nerves, vasculature or other tissue structures adjacent the bony portions on the approach to the space therebetween. Inserter instrument 20, 320 can also be employed as a guide to guide placement of instruments to prepare vertebrae or the adjacent bony portions to receive implant I. Various preparation instruments are contemplated that could be guided with inserter instrument 20, 320, including center-cut chisels, corner cut chisels, distractors, rasps, scrapers, and reamers, for example.

It is also contemplated that inserter instruments 20, 320 can be engaged to one or more of the vertebrae, adjacent bony portions, or other structure to maintain a positioning of inserter instruments 20, 320 as the implant is positioned between the bony portions and/or as one or more of the bony portions or vertebrae are prepared to receive the implant with preparation instruments. For example, as the implant I is positioned between the vertebrae, the implant may meet resistance to distal movement upon contact with the bony structure of the vertebrae, and such resistance may tend to displace inserter instrument 20, 320 proximally as increased force is applied to overcome the resistance. Various attachment arrangements are contemplated to maintain the positioning of inserter instrument 20, 320 relative to the vertebrae and facilitate insertion of the implants and/or instruments. Examples of such arrangements are provided U.S. patent application Ser. No. 11/112,586 filed on Apr. 22, 2005, which is incorporated herein by reference in its entirety.

Inserter instruments 20, 320 can protect the adjacent tissue and vasculature from the implant during insertion by preventing the spreader 60 and/or implant I from twisting and moving outside the guide path during insertion. The inserter instruments 20, 320 further protect the bony structures between which the implant is inserted during insertion, and facilitates withdrawal of the implant after it is positioned in the space between the bony structures. Furthermore, inserter instruments 20, 320 can be adapted to guide insertion of implants of various heights, and to provide varying spacing between adjacent bony portions customized to fit the particular implant. Inserter instruments 20, 320 can include a low profile in the operative space, facilitating visualization and placement of additional instruments in the operative approach to the bony structures. The inserter instruments can be disassembled, allowing for cleaning and use of selected guide members from a set of guide members, providing convenience and flexibility to the surgeon during the surgical procedure.

While the invention has been illustrated and described in detail in the drawings and foregoing description, the same is to be considered as illustrative and not restrictive in character. All changes and modifications that come within the spirit of the invention are desired to be protected.

What is claimed is:

1. A system for implant delivery to a space between adjacent bony portions, comprising:
    an implant positionable in the space;
    a handle assembly including a mounting portion and an actuating portion;
    a pair of opposing guide members coupled to said mounting portion, each of said guide members including a body extending along an insertion axis between a distal end and a proximal end and having an outer surface and an opposite guide surface, said guide surfaces being oriented toward one another and said distal ends are positionable in the space, wherein said proximal ends are pivotally coupled to said mounting portion in a corresponding recess of said mounting portion, and further comprising a spring in each recess extending between said mounting portion and a respective one of said guide members at a location proximal of said pivotal coupling of said respective guide member so that said springs bias said distal ends of said guide members toward one another about said pivotal coupling location, each of said guide members further including a projection at said proximal end thereof extending outwardly away from one another and projecting from said corresponding recess of said mounting portion to provide access to said guide member for applying a manual force to pivot said distal ends of said guide members away from one another;
    a spreader positioned between said pair of guide members, said spreader including a central body movable along said guide members between said distal and proximal ends with said implant positioned forwardly of said spreader; and
    a drive member assembly coupled to said handle assembly and said spreader, said drive member assembly including a drive member linearly movable along said insertion axis by operation of said actuating portion of said handle assembly, said drive member including a distal coupling portion at a distal end of said drive member having a cross-sectional shape that includes three overlapping circular portions with a middle circular portion being larger than circular portions on each side thereof, wherein said spreader includes a central bore for receiving said distal coupling portion of said drive member, said central bore including a proximal portion extending from a proximal opening of said central bore to a distal portion of said bore, said proximal portion having a shape that corresponds to said cross-sectional shape of said distal coupling portion so that said distal coupling portion passes linearly therethrough in a predetermined orientation of said drive member relative to said spreader, said distal portion of said central bore having an interrupted circular shape that receives and permits said distal coupling portion to rotate therein to a rotated position upon rotation of said drive member relative to said spreader to lock said drive member to said spreader, wherein said coupling portion cannot pass from said distal portion into said proximal portion of said central bore when in said rotated position.

2. The system of claim 1, wherein:
said guide members each include an elongated slot extending in the direction of the insertion axis and opening along said guide surface and said outer surface; and
said spreader includes a pair of opposite wings extending from said central body slidingly received in said slot of a corresponding one of said guide members.

3. The system of claim 1, wherein said mounting portion of said handle assembly includes a fixed handle part and a mounting part, said actuating portion being pivotally coupled to said mounting part and pivotal toward and away from said fixed handle part.

4. The system of claim 3, wherein said mounting part includes a central window opening transversely to said insertion axis and a first bore extending through a distal wall of said mounting part and a second bore extending through a proximal wall of said mounting part, said first and second bores being in communication with said window and said drive member extends through said first and second bores.

5. The system of claim 4, wherein:
said drive assembly includes a locking tab positioned about said drive member and frictionally engaging said drive member when obliquely oriented relative thereto, said locking tab being biased to said oblique orientation; and
said proximal wall of said mounting part includes a hook extending proximally from said proximal wall, said locking tab extending from said drive member to an end of said locking tab that engages said hook when said locking tab is in said oblique orientation.

6. The system of claim 5, wherein said drive assembly includes a driving tab positioned about said drive member in said window, said driving tab being biased toward said proximal wall to a first configuration orthogonally oriented to said drive member and being pivotable about said drive member with said actuating portion to frictionally engage said drive member and linearly and distally advance said drive member along said insertion axis as said actuating portion is pivoted toward said fixed handle part of said mounting portion of said handle assembly.

7. The system of claim 6, wherein said drive member includes a handle at a proximal end thereof proximal of said locking tab, said handle being operable to rotate said drive member and said coupling portion to said rotated position.

8. The system of claim 1, wherein said pair of guide members each include an abutment member adjacent said distal end thereof, said abutment member projecting from said outer surface of said respective guide member.

9. The system of claim 1, wherein said spreader includes a pair of distally extending engaging members positionable along opposite sides of said implant positioned between said guide members and distally of said spreader.

10. A system for implant delivery to a space between adjacent bony portions, comprising:
an implant positionable in the space;
a handle assembly including a mounting portion and an actuating portion;
a pair of opposing guide members coupled to said mounting portion, each of said guide members including a body extending along an insertion axis between a distal end and a proximal end and having an outer surface and an opposite guide surface, said guide surfaces being oriented toward one another and said distal ends are positionable in the space between adjacent bony portions, wherein said proximal ends are pivotally coupled to said mounting portion in a corresponding recess of said mounting portion, and further comprising a spring in each recess extending between said mounting portion and a respective one of said guide members at a location proximal of said pivotal coupling of said respective guide member so that said springs bias said distal ends of said guide members toward one another about said pivotal coupling location, each of said guide members further including a projection at said proximal end thereof extending outwardly away from one another and projecting from said corresponding recess of said mounting portion to provide access to said guide member for applying a manual force to pivot said distal ends of said guide members away from one another; and
a drive member assembly coupled to said handle assembly and including a drive member extending toward said implant between said guide members, said drive member being mounted to said mounting portion of said handle assembly, wherein said drive member assembly includes a driving tab coupled to said actuating portion of said handle assembly, said driving tab and said actuating portion being normally biased to a first position where said driving tab is orthogonally oriented to said insertion axis and said driving tab includes an end engaged to said actuating portion so that as said actuating portion is moved toward a second position said driving tab pivots about said drive member from said orthogonal orientation to engage said drive member with said driving tab to linearly advance said drive member along said insertion axis relative to said guide members, wherein said drive member includes a distal coupling portion having a cross-sectional shape that includes three overlapping circular portions with a middle circular portion being larger than circular portions on each side thereof, further comprising a spreader including a central bore for receiving said distal coupling portion of said drive member, said central bore including a proximal portion extending from a proximal opening of said central bore to a distal portion of said bore, said proximal portion having a shape that corresponds to said cross-sectional shape of said distal coupling portion so that said distal coupling portion passes linearly therethrough in a predetermined orientation of said drive member relative to said spreader, said distal portion of said central bore having an interrupted circular shape that receives and permits said distal coupling portion to rotate therein to a rotated position upon rotation of said drive member relative to said spreader to lock said drive member to said spreader, wherein said coupling portion cannot pass from said distal portion into said proximal portion of said central bore when in said rotated position.

11. The system of claim 10, further comprising a spring about said drive member extending between said drive member and a distal wall of said mounting portion to bias said driving tab to said first position toward a proximal wall of said mounting portion.

12. The system of claim 11, wherein said distal wall and said proximal wall each include a bore along said insertion axis through which said drive member extends.

13. The system of claim 12, wherein said spring and said driving tab are housed in a laterally opening window of said mounting portion and said proximal and distal bores are in communication with said window.

14. The system of claim 10, wherein said mounting portion includes a mounting part and a fixed handle part, said actuating portion being pivotally coupled to said mounting part and being movable toward said fixed handle part to pivot said driving tab from said first position.

15. The system of claim 10, wherein said spreader is positioned between said pair of guide members, said spreader including a central body movable along said guide members in the direction of said insertion axis between said distal and proximal ends, wherein:
    said guide members each include an elongated slot extending along said insertion axis and opening along said guide surface and said outer surface; and
    said spreader includes a pair of opposite wings extending from said central body slidingly received in said slot of a corresponding one of said guide members.

16. The system of claim 10, wherein:
    said drive member assembly includes a locking tab positioned about said drive member and frictionally engaging said drive member when obliquely oriented relative thereto, said locking tab being biased to said oblique orientation; and
    said proximal wall of said mounting part includes a hook extending proximally from said proximal wall, said locking tab extending from said drive member to an end of said locking tab that engages said hook when said locking tab is in said oblique orientation.

17. The system of claim 16, wherein said locking tab is pivotal against said bias to an unlocked position having a generally orthogonal orientation relative to said drive member, said drive member being freely movable relative to said locking tab and said mounting portion of said handle assembly when said locking tab is in said unlocked position.

18. A system for implant delivery to a space between adjacent bony portions, the system comprising:
    a pistol-grip type handle assembly including a mounting portion and an actuating portion, the mounting and actuating portions rotatably coupled together;
    a pair of opposed elongate guide members rotatably coupled to the mounting portion, each of the guide members including a distal end adapted to be positioned in the space and an opposite proximal end rotatably coupled to said mounting portion in a corresponding recess of said mounting portion, and further comprising a spring in each recess extending between said mounting portion and a respective one of said guide members at a location proximal of said pivotal coupling of said respective guide member so that said springs bias said distal ends of said guide members toward one another about said pivotal coupling location, each of said guide members further including a projection at said proximal end thereof extending outwardly away from one another and projecting from said corresponding recess of said mounting portion to provide access to said guide member for applying a manual force to pivot said distal ends of said guide members away from one another;
    a spreader disposed between the guide members; and
    a drive member assembly coupled to the handle assembly and the spreader, the drive member assembly including a drive member axially movable towards the guide member distal ends upon rotational actuation of the handle assembly actuating portion, wherein said drive member assembly extends toward said distal end of said guide members, said drive member being mounted to said mounting portion of said handle assembly, wherein said drive member assembly includes a driving tab coupled to said actuating portion of said handle assembly, said drive member assembly including a spring about said drive member that normally biases said driving tab and said actuating portion to a first position where said driving tab is generally orthogonally oriented to said insertion axis and said driving tab includes an end engaged to said actuating portion so that as said actuating portion is moved toward a second position said driving tab pivots about said drive member and against said bias of said spring from said generally orthogonal orientation to positively engage said drive member to axially move said drive member toward said distal ends of said guide members, wherein said drive member includes a distal coupling portion having a cross-sectional shape that includes three overlapping circular portions with a middle circular portion being larger than circular portions on each side thereof, wherein said spreader includes a central bore for receiving said distal coupling portion of said drive member, said central bore including a proximal portion extending from a proximal opening of said central bore to a distal portion of said bore, said proximal portion having a shape that corresponds to said cross-sectional shape of said distal coupling portion so that said distal coupling portion passes linearly therethrough in a predetermined orientation of said drive member relative to said spreader, said distal portion of said central bore having an interrupted circular shape that receives and permits said distal coupling portion to rotate therein to a rotated position upon rotation of said drive member relative to said spreader to lock said drive member to said spreader, wherein said coupling portion cannot pass from said distal portion into said proximal portion of said central bore when in said rotated position.

19. The system of claim 18, wherein:
    said drive member assembly includes a locking tab positioned about said drive member and frictionally engaging said drive member when obliquely oriented relative thereto, said locking tab being biased to said oblique orientation; and
    said proximal wall of said mounting part includes a hook extending proximally from said proximal wall, said locking tab extending from said drive member to an end of said locking tab that engages said hook when said locking tab is in said oblique orientation.

20. The system of claim 19, wherein said locking tab is pivotal against said bias to an unlocked position having a generally orthogonal orientation relative to said drive member, said drive member being freely movable relative to said locking tab and said mounting portion of said handle assembly when said locking tab is in said unlocked position.

* * * * *